United States Patent
Feeback et al.

[11] Patent Number: 6,107,081
[45] Date of Patent: Aug. 22, 2000

[54] UNI-DIRECTIONAL CELL STRETCHING DEVICE

[75] Inventors: Daniel L. Feeback, Houston; Mark S. F. Clarke, League City, both of Tex.

[73] Assignee: The United States of America as represented by the Administrator of the National Aeronautics and Space Administration, Washington, D.C.

[21] Appl. No.: 09/245,950

[22] Filed: Feb. 5, 1999

[51] Int. Cl.[7] ............................................. A01N 1/00
[52] U.S. Cl. ............................... 435/284.1; 435/289.1; 435/286.1
[58] Field of Search ................ 435/286.1, 286.2, 435/284.1, 289.1; 73/788, 807, 815, 816, 817, 826, 837, 856

[56] References Cited

U.S. PATENT DOCUMENTS

| | | | |
|---|---|---|---|
| 4,456,683 | 6/1984 | Lintilhac et al. | 435/3 |
| 4,839,280 | 6/1989 | Banes | 435/285 |
| 4,851,354 | 7/1989 | Winston et al. | 435/284 |
| 4,901,581 | 2/1990 | Fain et al. | 73/795 |
| 4,940,853 | 7/1990 | Vandenburgh | 435/240.23 |
| 5,002,377 | 3/1991 | Battifora et al. | 350/535 |
| 5,217,899 | 6/1993 | Shapiro et al. | 435/284 |
| 5,293,703 | 3/1994 | Coste et al. | 38/102.4 |
| 5,348,879 | 9/1994 | Shapiro et al. | 435/240.241 |
| 5,406,853 | 4/1995 | Lintilhac et al. | 73/789 |
| 5,486,457 | 1/1996 | Butler et al. | 435/7.2 |
| 5,589,646 | 12/1996 | Khachaturian et al. | 73/862.474 |

OTHER PUBLICATIONS

Sadoshima et al., Journal of Biological Chemistry, May 25, 1992, pp. 10551–10560.
Vandenburgh, In Vitro Cellular & Developmental Biology, Jul. 1988, pp. 609–619.
Clarke et al., FASEB, Mar. 1996, 502–509.

*Primary Examiner*—David A. Redding
*Attorney, Agent, or Firm*—James M. Cate

[57] ABSTRACT

The present invention relates to an apparatus and method for applying various degrees of linear, mechanical loads on mammalian tissues, and in particular, for effecting linear stretching of tissue and simulating changes in hydrostatic pressures encountered during tissue contraction in vivo. The apparatus is useful for the study of mechanical loading in human tissue, and specifically, for permitting the evaluation of the effects of mechanical loading of skeletal or cardiac tissue and of the effects of removal of mechanical loading due to inactivity or the like, and the subsequent reapplication of load to these tissues.

24 Claims, 5 Drawing Sheets

UNI-DIRECTIONAL CELL STRETCHING DEVICE

ORIGIN OF THE INVENTION

The invention described herein may be manufactured and used by or for the Government of the United States ot America for governmental purposes without the payment of any royalties thereon or therefor.

BACKGROUND OF THE INVENTION

1. Field of the Invention

The present invention relates generally to the fields of aerospace physics and physiology. More specifically, the present invention relates to a uni-directional cell stretching device which is capable of mimicking the linear load profiles placed on skeletal muscle within the human body.

2. Description of the Related Art

The physiological responses of the living organism to mechanical loading are numerous and varied. One area of special interest to NASA is the effect of mechanical loading on human muscle tissue, specifically the response of skeletal or cardiac muscle tissue to the removal of mechanical load during space flight and the re-application of mechanical load to these tissues on return to the gravitational field of earth or a distant planet. The use of animal and human models to study the effects of mechanical load/unloading on muscle tissue are useful up to a point, but the basic cellular events involved in microgravity-induced muscle atrophy and re-adaptation to terrestrial gravity need to be studied in isolation from the complex set of load-induced responses generated in the whole organism.

One way of examining microgravity-induced muscle atrophy and re-adaptation to terrestrial gravity is to study purified cultured muscle cells in a mechanically active tissue culture environment designed to mimic physiological loading conditions. By utilizing a system which allows the continuous application of mechanical load to cultured cells, the effects of unloading can also be studied. This can be achieved by loading cells for a set period of time (i.e., 10 days) and then removing that load stimulus so as to study the effects of unloading. Load can then be reapplied to the cells in order to study the re-adaptation response to loading after a period of unloading. Such a system, in conjunction with the use of human muscle cells, has clear modeling potential for studying the effects of microgravity (i.e., unloading) and terrestrial re-adaptation (i.e., return to earth) on the basic cellular processes involved in the response of human muscle tissue to such stimuli, a set of responses which are at this time unclear.

There are several commercial cell stretching systems available currently. All of these systems utilize a deformable culture substratum on which the cells of interest are grown. The culture substratum used is invariably an elastic silicone polymer coated with a physiological extracellular matrix compound to enable cell attachment.

One cell stretching system (Sadoshima et al., 1991) uses a sheet of silicone which is stretched by means of a ratchet/frame assembly attached to one end of the sheet. The whole assembly is immersed in tissue culture medium. This system is capable of producing linear stretch on the growing cells but has several disadvantages surrounding the design. First, to increase the amount ot load on the cells the whole assembly must be removed from the medium container and the frame/ratchet moved; second, removal of the assembly from the medium disturbs the cells and can lead to bacterial or fungal contamination and third, the amount of load placed on the cells is directly proportional to the position of ratchet used and hence load application is step-wise rather than continual.

A second cell stretching system, the Mechanical Cell Stimulator (Vandenburgh, 1988) utilizes a circular deformable membrane on which the cells grow but employs a metal pin to stretch the substratum by way of a linear actuator stepper motor lifting the pin up into the center of the membrane. This device allows a continuous load to be applied to the cells but the type of stretch applied to the cells is both linear and radial, the latter of which is non-physiological load stimulus in the case of skeletal muscle. A second problem with this device is the electromagnetic field generated around the cells by the stepper motor, a potential confounding stimulus on the cells.

A third cell stretching system, namely the Flexercell Strain Unit™ (Clarke et al., 1996), uses a similar round configuration for its deformable membrane incorporated into the base of a tissue culture plate except that it is stretched downwards by the application of vacuum to the underside of the membrane. This technique also has the disadvantage of production of non-physiological radial loading. All of the devices listed above have a common problem in that the whole device must be placed inside a tissue culture incubator with associated control units being placed outside the incubator.

The prior art is deficient in the lack of a cell stretching device which is capable of mimicking the unique linear loading profiles placed on a large number of human cells. Further, the prior art is deficient in the lack of real-time viewing of the cellular loading/unloading response of human cells. The present invention fulfills this long-standing need and desire in the art.

SUMMARY OF THE INVENTION

The present invention is directed to a uni-directional cell stretching device capable of mimicking the linear loading profiles placed on skeletal muscle within the human body. The design also allows either interval or continuous stretching in a single direction or a linear "flexing" profile by intermittent reversal of the ram direction. Microprocessor control of either the fluid-filled ram or stepper motor screw drive configuration allows precise control of the amount of load placed upon the cells. In addition, the stand alone design allows the device to be used outside of a tissue culture incubator. The addition of fiber optic ports allows real-time viewing of the cellular loading/unloading responses as well as the option for time lapse observation. Medium exchange/medium sampling ports allow the study of factors released into the medium by the cells as a consequence of loading/unloading.

In one embodiment of the present invention, there is provided a uni-directional cell stretching device capable of mimicking linear loading profiles, comprising a ram, at least one strip, a tissue culture vessel, a sealed chamber and a mechanical pump. Preferably, the strips are connected to the ram by removable pins through a cylindrical tube support to form a ram assembly. The strips are elastic, suitably of silicon, and coated with an extra-cellular matrix upon which tissue cultured cells are grown and stretched. Still preferably, the pump is microprocessor-controlled and controls the amount of load placed upon the cells. Further, the ram preferably moves bi-directionally in a single plane in an interval or continuous mode. Such a movement is driven by injecting a sterile fluid into the sealed chamber of the ram using the mechanical pump.

In another embodiment of the present invention, there is provided a uni-directional cell stretching device capable of mimicking linear loading profiles, comprising a ram, at least one strip, a tissue culture vessel, optical ports and medium exchange/medium sampling ports. The strips are connected to the ram forming a linear stepper motor/screw drive assembly, which drives the movement of the ram, further controls the amount of load placed upon the cells. Preferably, the tissue culture vessel contains a tissue culture medium which is heated by a piezoelectric-heating jacket. More preferably, the optical ports allow real-time viewing of the cellular loading/unloading responses of the cells.

In yet another embodiment of the present invention, there is provided a method of applying linear load profiles on human or non-human cells in culture by placing the cells in the above claimed uni-directional cell stretching device(s). Representative cells which can can be examined using this technique include skeletal muscle cells, cardiac muscle cells, endothelial cells, vascular smooth muscle cells and chondrocytes.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the functional prototype design 1 of the uni-directional cell stretcher.

The silicon strips 8 on which the cells are grown are attached to the ram assembly by means of support pins 6 inserted through the ram assembly (FIG. 1A) and the cylindrical support tube 13 of the silicon strip assembly (FIG. 1C). Gas exchange occurs through the gas-permeable membrane 5 located at the top of the tissue culture vessel 9.

Controlled stretching of the silicon strip or strips 8 and by extension the cells 11 grown on their surface is achieved by increasing or decreasing the hydraulic pressure generated by a pump 3 within the hydraulic compression chamber 4, thereby moving the ram 7 in a uni-directional fashion. As the silicon strips are attached at one end to the stationary ram assembly (FIG. 1A) and at the other to the end of the telescopic ram 7, the movement of the ram 7 in either direction is translated to a defined amount of stretch on the silicon strip 8.

FIG. 3 are photographs of the functional prototype uni-directional cell stretching device.

FIG. 4 shows the micrographs of skeletal muscle cells grown in the prototype uni-directional cell stretching device.

DETAILED DESCRIPTION OF THE INTENTION

As used herein, "uni-directional" means movement within a single plane or axis in a positive or negative direction along a single vector.

As used herein, "linear load profiles" means mechanical loading which occurs in a single plane or axis during contraction of muscular tissue from tendon to tendon or compression of bone tissue from joint to joint.

As used herein, "cell stretching" means elongation of tissue cultured cells by virtue of deforming the culture substratum to which the cells are attached.

As used herein, "mechanical load/unload" means applying or removing physical stretch on tissue cultured cells.

As used herein, "ram" means a telescopic structure capable of transmitting mechanical force by means of either mechanical or electromechanical movement.

As used herein, "ram assembly" means the complete ram and hydraulic compression chamber to which are attached silicon strips by means of integral cylindrical support tubes held in position to the ram assembly by removable support pins.

As used herein, "strip" means a flat silicon polymer fashioned in a rectangular form to which plastic support tubes have been sewn or otherwise affixed at opposite ends.

As used herein, "support structure" means a structure, e.g., the ram assembly, which provides a physical anchorage point for the strip.

As used herein, "extracellular matrix" means extracellular materials produced and secreted by cells (or synthetic compounds which mimic these materials) which act as a cellular cement or adhesive between cells and the surface of the culture substratum, in this case the culture substratum being the silicon strip.

As used herein, "support pins" means cylindrical or rectangular pins (made from a solid material such as metal or ceramic) used to attach the silicon strips to the ram assembly.

As used herein, "linear stretch" means stretch in a uni-directional manner along a single plane or axis defined by a positive or negative vector.

As used herein, "deformable membrane" means a membrane which can be physically deformed or stretched due to its inherent elastic properties.

As used herein, "real time viewing" means direct, immediate observation of live cells without the need to remove the cells from the culture vessel.

The present invention relates to an apparatus and method for applying various degrees of linear, mechanical loads on human muscle tissue, and in particular, for effecting linear stretching of muscle tissue, simulating changes in hydrostatic pressures encountered during muscle contraction in vivo. The apparatus is useful for the study of mechanical loading in human muscle tissue, and specifically, for permitting the evaluation of the effects of mechanical loading on skeletal or cardiac tissue and of the effects of the removal of mechanical loading due to inactivity or the like, and the subsequent reapplication of load to these tissues.

The unique linear loading profile obtained using the present device removes confounding load vectors, such as radial stretch or compression from experiments involving mechanical loading. In addition to skeletal muscle cells, various other human cells which exist in a mechanically active environment, such as endothelial cells, vascular smooth muscle cells, cardiac muscle cells and chondrocytes, can be cultured in the present device.

In one embodiment of the present invention, there is provided a uni-directional cell stretching device capable of mimicking linear loading profiles, comprising a ram, at least one strip, a tissue culture vessel, a sealed chamber and a mechanical pump.

In one preferred embodiment, an elongated stretching mechanism is provided in which a drive mechanism is drivingly connected with a linearly displaceable ram member and operable for driving the ram linearly outwardly from a relatively fixed support structure. The elastic strip, suitably of silicon, is coated with an extra-cellular matrix upon which the tissue cultured cells are deposited. The strips are connected to the ram by removable support pins through a cylindrical tube support to form a ram assembly, whereby when the ram is driven outwardly, the elastic strips are caused to stretch longitudinally, thereby stretching the tissue cultured cells which are deposited on the extra-cellular matrix.

In another preferred embodiment of the present invention, the pump is microprocessor-controlled and controls the amount of load placed upon the cells. The ram moves bi-directionally in a single plane in an interval or continuous mode driven by injecting a sterile fluid into the hydraulic compression chamber of the ram assembly using the mechanical pump.

In another embodiment of the present invention, there is provided a uni-directional cell stretching device capable of mimicking linear loading profiles, comprising a ram, at least one strip, a tissue culture vessel, optical ports and medium exchange/medium sampling ports. The strips are connected to the ram forming a linear stepper motor/screw drive assembly, which drives the movement of the ram, further controls the amount of load placed upon the cells. Preferably, the tissue culture vessel contains a tissue culture medium which is heated by a piezoelectric-heating jacket. Still preferably, the optical ports allow real-time viewing of the cellular loading/unloading responses of the cells.

In yet another embodiment of the present invention, there is provided a method of applying linear load profiles on human or non-human cells in culture by placing the cells in the above claimed uni-directional cell stretching device(s). Preferably, the cells can be skeletal muscle cells, cardiac muscle cells, endothelial cells, vascular smooth muscle cells, or chondrocytes.

The following examples are given for the purpose of illustrating various embodiments of the invention and are not meant to limit the present invention in any fashion.

EXAMPLE 1

Functioning Prototype Design

The device of the present invention can be readily understood, created and used as described below and with reference to the attached figures. For example, FIG. 1 shows the functional prototype design 1 of uni-directional cell stretcher, consisting of a microprocessor-controlled mechanical pump 3, a fluid reservoir 4, gas-permeable membrane 5, removable support pins 6, ram 7, extracellular-matrix-coated elastic silicon strips 8, a sealed culture vessel 9, a tissue culture medium reservoir 10, non-stretchable plastic sheeting 12, a cylindrical support tube 13 and nylon threaded cross stitching 14. 11 indicates tissue cultured cells.

Figures 1A, 1C:
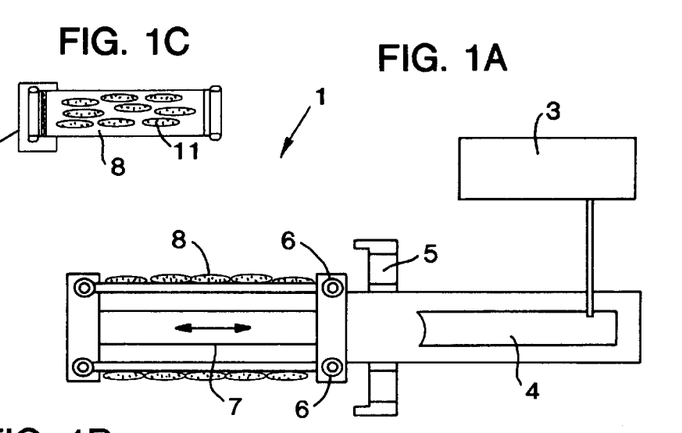
FIG. 1A: the overall design 1.
FIG. 1C: the top view of the portion consisting of the extracellular-matrix-coated elastic silicon strips 8.
Figure 1B:
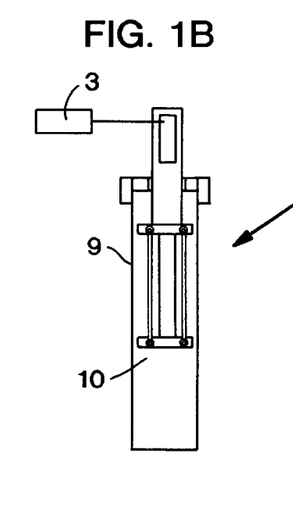
FIG. 1B: the ram assembly (underlined portion) consisting of the ram 7 and hydraulic compression chamber 4 was inserted into the tissue culture vessel 9, which contains a tissue culture medium 10.
Figure 1D:
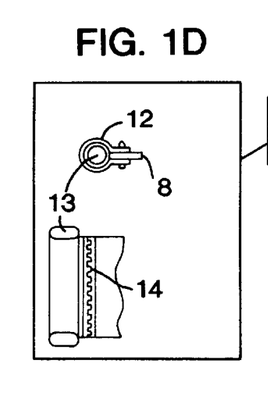
FIG. 1D: an enlarged view of the boxed portion of FIG. 1C, demonstrating a cylindrical support tube 13 and nylon threaded cross stitching 14; and a cross section of the boxed portion of FIG. 1C, demonstrating non-stretchable plastic sheeting 12, a cylindrical support tube 13 and extracellular-matrix-coated elastic silicon strips 8, on which cells 11 are grown.

FIG. 1 shows the functional prototype design 1 of the uni-directional cell stretcher. FIG. 1A shows the overall design 1. FIG. 1B shows that the ram assembly (underlined portion) was inserted into the tissue culture vessel 9, which contains a tissue culture medium 10. FIG. 1C shows the top view of the portion consisting of the extracellular-matrix-coated elastic silicon strips 8. FIG. 1D shows an enlarged view of the boxed portion of FIG. 1C, demonstrating a cylindrical support tube 13 and nylon threaded cross stitching 14; and a cross section of the boxed portion of FIG. 1C, demonstrating non-stretchable plastic sheeting 12, a cylindrical support tube 13 and extracellular-matrix-coated elastic silicon strips 8.

The silicon strips 8 on which the cells are grown are attached to the ram assembly by means of support pins 6 inserted through the ram assembly (FIG. 1A) and the cylindrical support tube 13 of the silicon strip assembly (FIG. 1C). Gas exchange occurs through the gas-permeable membrane 5 located at the top of the tissue culture vessel 9.

Controlled stretching of the silicon strip or strips 8 and by extension the cells 11 grown on their surface is achieved by increasing or decreasing the hydraulic pressure generated by a pump 3 within the hydraulic compression chamber 4, thereby moving the ram 7 in a uni-directional fashion. As the silicon strips are attached at one end to the stationary ram assembly (FIG. 1A) and at the other to the end of the telescopic ram 7, the movement of the ram 7 in either direction is translated to a defined amount of stretch on the silicon strip 8.

Figure 2:
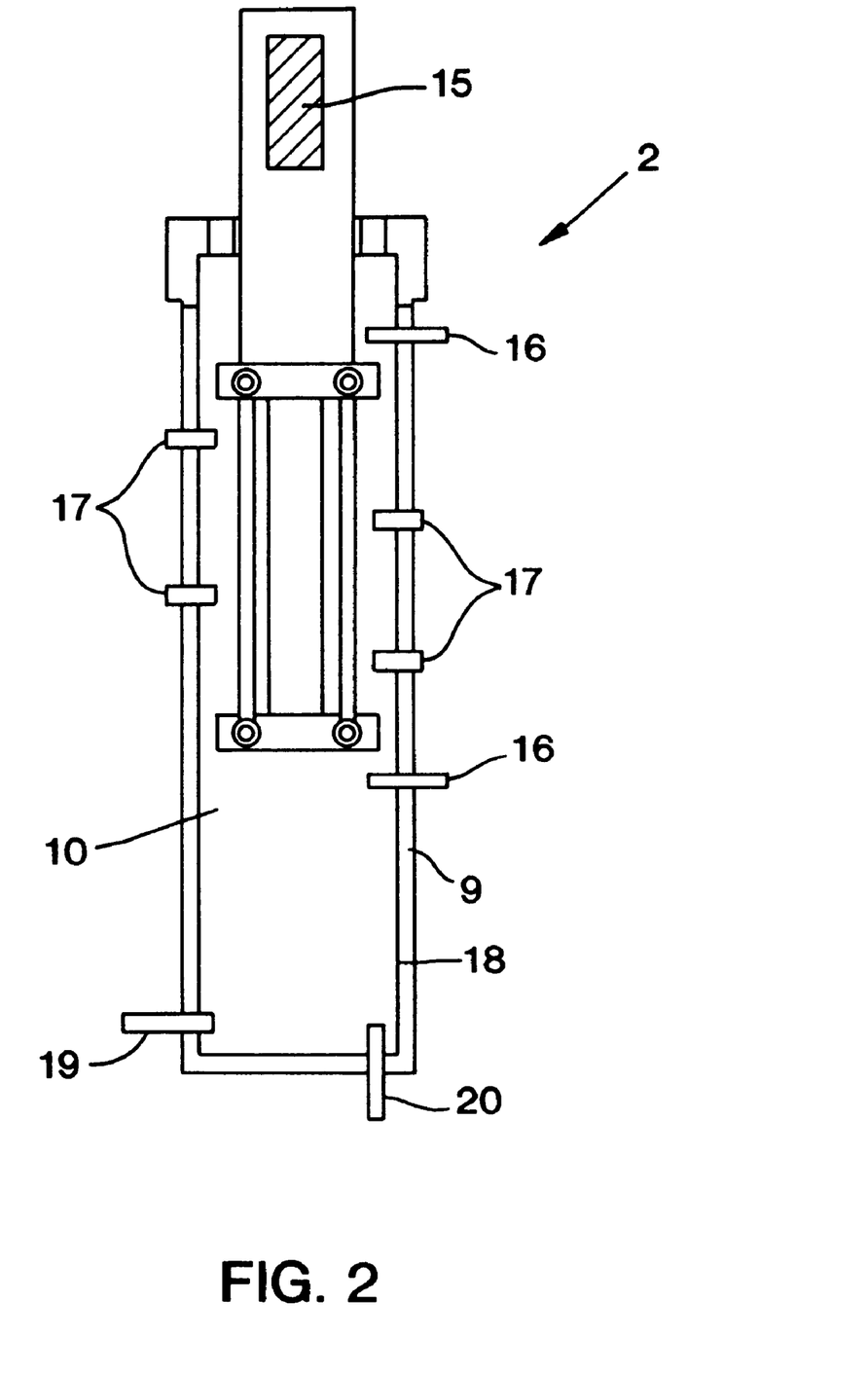
FIG. 2 shows the advanced stand alone design 2 of uni-directional cell stretcher, consisting of a stepper motor/screw drive assembly 15, temperature/gas sensors 16, optical ports 17, a sealed culture vessel 9, a tissue culture medium reservoir 10, a piezoelectric-heating jacket 18, a medium exchange port 19, and a $CO_2$/air inlet 20.

FIG. 2 shows the advanced stand alone design 2 of uni-directional cell stretcher, consisting of a stepper motor/screw drive assembly 15, temperature/gas sensors 16, optical ports 17, a sealed culture vessel 9, a tissue culture medium reservoir 10, a piezoelectric-heating jacket 18, a medium exchange port 19. and a CO2/air inlet 20.

Figure 3A:
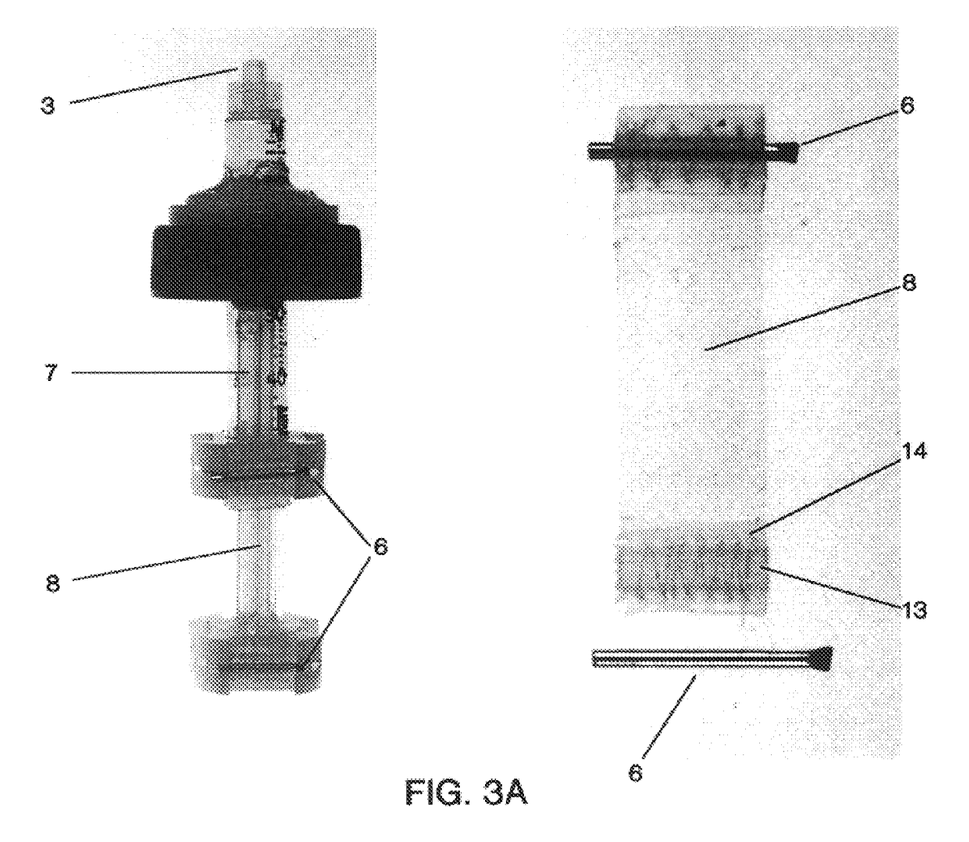
FIG. 3A shows disassembled ram assembly illustrating the configuration of the silicone strip (coated with extracellular material) on which the cells are grown. Cell seeding is carried out in a standard culture petri-dish prior to strip being inserted on the ram.
Figure 3B:
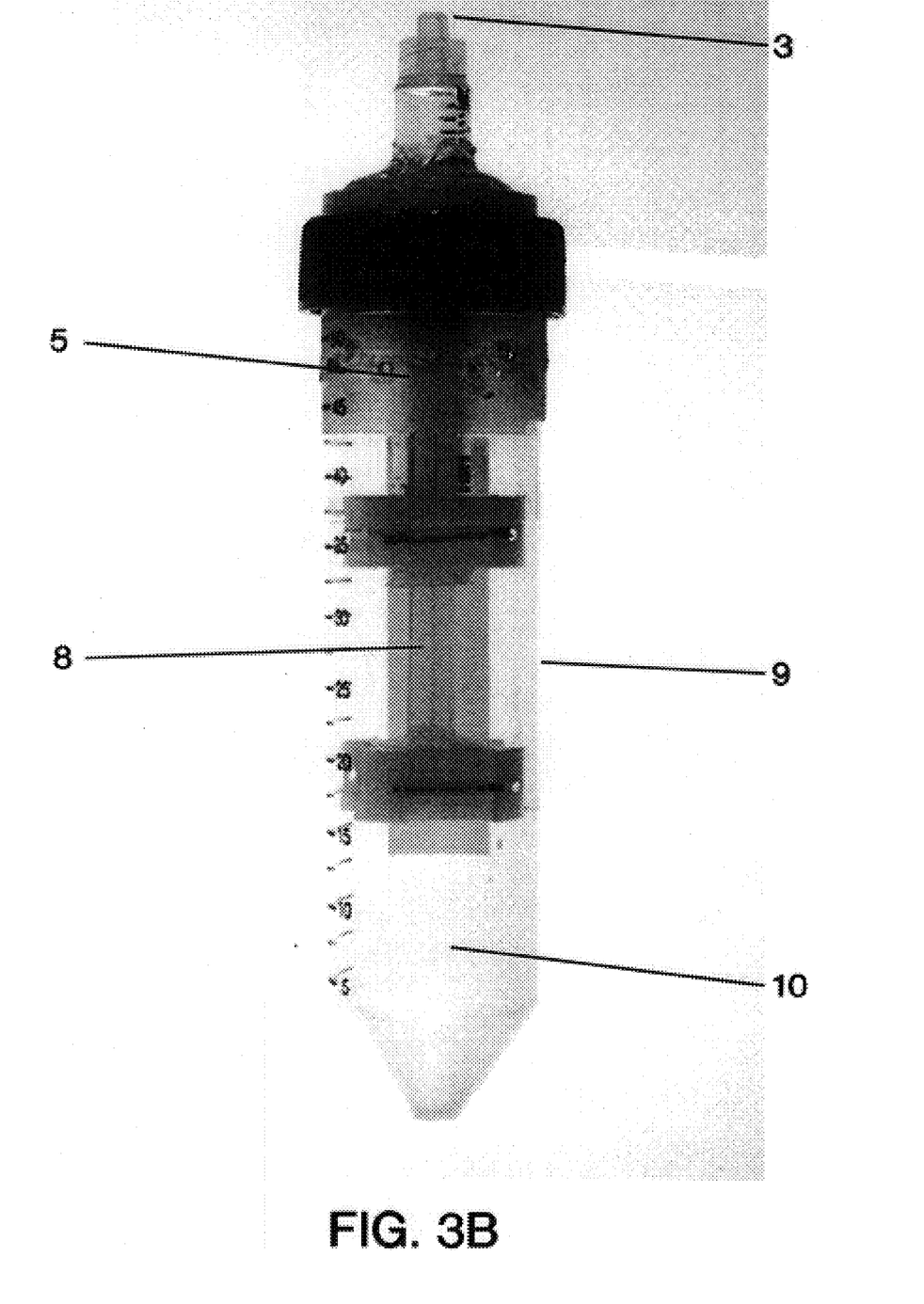
FIG. 3B shows assembled device illustrating culture vessel/tissue culture medium in which cells are grown while being stretched.

The cell stretcher disclosed in the present study has been designed to produce only linear stretch on cells grown on a deformable membrane. Instead of a round configuration for the deformable membrane, a strip design has been used, again coated with biological culture substratum (e.g., collagen Type I). The strips 8 are attached by removable support pins 6 through a cylindrical support tube 13 attached at each end of the strips to a ram assembly 1 (FIGS. 1 and 3).

This configuration allows the cells to be grown on the strips in standard tissue culture plates to the required cell density or differentiation state prior to placing the strip in the cell stretcher. This configuration also has the added advantage of easy removal of the cells at the end of the loading experiment for microscopic examination (i.e., strip provides a planar surface for viewing) or biochemical analysis (i.e., cells can be easily removed from the strip by ultrasonic or detergent solubilization). The strips are arranged in a circular fashion around the ram. The ram assembly is then inserted into a tissue culture vessel 9 containing culture medium 10 (FIGS. 1 and 3). The movement of the ram is controlled by the injection of a sterile fluid into the hydraulic compression chamber 4 behind the ram 7 using a microprocessor-controlled mechanical pump 3. Movement of the ram is bi-directional in a single plane and as a consequence the cells are stretched in a linear direction, thereby mimicking physiological loading conditions. Reversal of the injection flow results in unloading of the cells by decreasing the stretch placed on the strip. In the embodiment of FIG. 1, the rate of stretching is controlled by liquid flow rate under microprocessor control into, or out of, the ram hydraulic compression chamber 4. A simple analogy is to a fluid-filled hypodermic syringe where the movement of the plunger is determined by how much liquid is in the barrel of the syringe. This design in its simplest configuration can be housed in a tissue culture incubator with the mechanical pump 3 placed outside the incubator (FIGS. 1 and 3).

EXAMPLE 2
Advanced Stand Alone Design

A second embodiment of the device of the present invention utilizes a microprocessor-controlled linear stepper motor/screw drive assembly 15 to advance or reverse the ram (FIG. 2). The functioning prototype design described has utilized the fluid-filled ram configuration. In addition, the design also describes the use of a stand-alone unit which is temperature controlled with integral ports for medium exchange or medium sampling and gas infusion to achieve optimal cell growth conditions. As the stand-alone device functions as a sealed unit, intra-vessel pressure can be altered within the ranges found within muscle tissue in vivo, hence mimicking changes in hydrostatic pressures encountered during muscle contraction in the whole animal. This version of the design also incorporates miniature fiber optic units 17 to allow real time imaging of the cells during the loading procedure, a distinct advantage over existing technologies where the cells have to be removed from the loading device before viewing.

EXAMPLE 3
Human Skeletal Muscle Cells (HSkMC)

Human skeletal muscle cells were obtained from the Clonetics Corporation (San Diego, Calif.). Dulbecco's modified Eagles' medium (DMEM)/F12 medium, trypsin/EDTA solution, and Dulbecco's phosphate-buffered saline (D-PBS) were all obtained from Gibco-BRL (Grand Island, N.Y.). Epidermal growth factor, insulin, fetuin, and bovine serum albumin (BSA) were all purchased from the Clonetics Corporation.

EXAMPLE 4
Cell Culture

HSkMC cells where grown in DMEM/F12 medium containing 5% fetal calf serum (FCS), 5 ng/ml epidermal growth factor, 20 (1 insulin, 2 (g/ml fetuin, and 100 (g/ml bovine serum albumin in a humidified 5% $CO_2$ atmosphere. The medium was exchanged for F12/DMEM medium containing 5% horse serum (HS) to initiate differentiation of myoblasts into myotubes. Alternatively, they were maintained in DMEM/F12 medium containing 5% FCS in order to promote proliferation and delay differentiation.

Figure 4A:
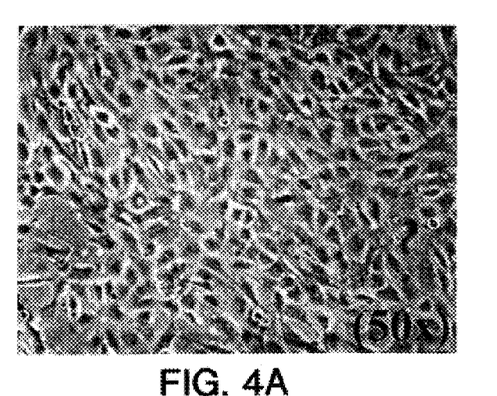
FIG. 4A shows skeletal muscle cells grown for 7 days in differentiation medium (2% horse serum) without stretch. Very little directional organization or myotube formation is noted.
Figure 4B:
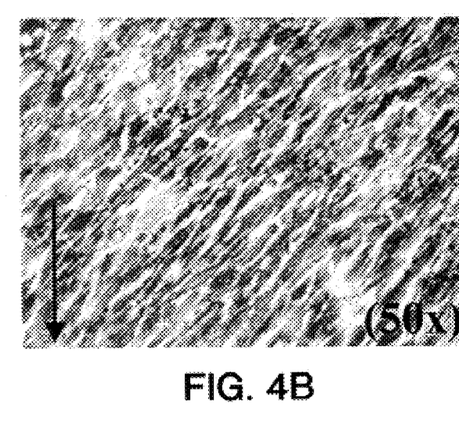
FIG. 4B shows skeletal muscle cells grown for 7 days in differentiation medium (2%, horse serum) with continuous stretching from 0 to 20% stretch at a rate of 2.85% stretch/day. Directional organization toward direction of stretch is noted.
Figure 4C:
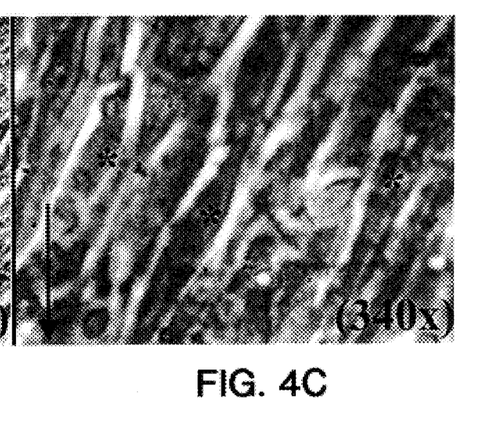
FIG. 4C shows high power magnification of stretched cells illustrating the presence of multi-nucleated myotube structures analogous to myofibers in vivo.

EXAMPLE 5
Response of Skeletal Muscle Cells Grown in the Uni-Directional Cell Stretcher Skeletal muscle cells were grown for 7 days in differentiation medium (2% horse serum) with or without intermittent stretching of the cultures using the uni-directional cell stretcher. The degree of myoblast differentiation into myotubes was assessed by direct microscopic examination (FIG. 4). Very little directional organization or myotube formation occurred when no stretching was applied (FIG. 4A), while directional organization toward direction of stretch was observed when continuous stretching was applied from 0 to 20% stretch at a rate of 2.85% stretch/day (FIG. 4B). A higher power magnification illustrates the formation of multi-nucleated myotube structures which are analogous to myofibers in vivo (FIG. 4C).

Discussion

The present device is capable of mimicking the linear load profiles placed on skeletal muscle within the human body. Such a device will allow the study of the effect of mechanical load upon muscle cells, a basic research question of great importance to manned space flight. The present device can also be used to study a variety of biological questions of interest to numerous scientific researchers as is evidenced by the increasing demand for commercially available mechanically-active tissue culture environments like the Flexercell Strain Unit™.

The following references were cited herewith.

Sadoshima et al., 1991, J. of Biological Chemistry, 267: 10551–10560.

Vandenburgh, 1988, In Vitro Cellular & Dev. Biology, 24: 609–619.

Clarke et al., 1996, FASEB, 10: 502–509.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A uni-directional cell stretching device capable of mimicking linear tissue loading profiles, comprising:

a tissue culture vessel;

an actuator assembly, including a relatively fixed structure and an axially translatable ram within said vessel;

at least one elastic strip having one end portion removably connected to said ram and another, opposite end portion removably connected to said relatively fixed structure, said elastic strip being coated with an extra-cellular matrix; and driving means for axially translating said ram relative to said relatively fixed structure, and for axially translating said one end portion of said elastic strip affixed to said ram relative to said another, opposite end portion, for longitudinally stretching said at least one elastic strip.

2. The device of claim 1, wherein said driving means comprises a pump, a sealed piston chamber receiving a proximal end portion of said ram, and means for conducting fluid under pressure from said pump to said piston chamber for driving said ram.

3. The device of claim 2, wherein said chamber is filled with a sterile fluid.

4. The device of claim 1, wherein said at least one strip is connected to said ram by removable support pins extending within a cylindrical tube support.

5. The device of claim 1, wherein said at least one strip is a silicon strip.

6. The device of claim 1, wherein said tissue culture vessel contains tissue cultured cells grown and stretched on said at least one strip.

7. The device of claim 1, wherein said tissue culture vessel contains a tissue culture medium.

8. The device of claim 1, wherein said pump is microprocessor-controlled.

9. The device of claim 7, wherein said pump controls the amount of load placed upon cells.

10. The device of claim 1, wherein said ram moves bi-directionally in a single plane in an interval or continuous mode.

11. The device of claim 2, wherein said ram is driven by injecting a sterile fluid into said chamber using said pump.

12. The device of claim 1, wherein said driving means comprises a controllable motor and gearing means drivingly connecting said motor with said ram.

13. The device of claim 12, wherein said motor comprises a linear stepper motor and wherein said gearing means comprises a screw drive assembly.

14. A uni-directional cell stretching device capable of mimicking linear loading profiles, comprising:
    a ram having distal and proximal end portions and a piston chamber portion receiving said ram proximal end portion;
    at least one elastic strip, wherein said at least one strip is connected to said distal end portion of said ram;
    driving means for axially translating said ram while said strip is connected thereto, and for stretching said strip longitudinally by movement of said ram;
    a tissue culture vessel containing said strip;
    optical ports formed in said culture vessel; and
    medium exchange/medium sampling ports communicating through said culture vessel.

15. The device of claim 14, wherein said driving means comprises a linear stepper motor and screw drive assembly.

16. The device of claim 15, wherein said stepper motor/screw drive assembly controls the amount of load placed upon cells on said strip.

17. The device of claim 14, wherein said tissue culture vessel contains a tissue culture medium, further comprising a piezoelectric-heating jacket arranged for heating said medium.

18. The device of claim 14, wherein said optical ports allow real-time viewing of cells.

19. A method of applying linear load profiles on cells in culture, comprising the step of:
    placing said cells on said strip in the uni-directional cell stretching device of claim 1.

20. The method of claim 19, wherein said cells are selected from the group consisting of skeletal muscle cells, cardiac muscle cells, endothelial cells, vascular smooth muscle cells and chondrocytes.

21. A method of applying linear load profiles on cells in culture, comprising the step of:
    placing said cells in the uni-directional cell stretching device of claim 14.

22. The method of claim 21, wherein said cells are selected from the group consisting of skeletal muscle cells, cardiac muscle cells, endothelial cells, vascular smooth muscle cells and chondrocytes.

23. The method of claim 21, comprising the steps of axially translating said ram while said strip is connected thereto for stretching said strip longitudinally by movement of said ram; and removing said strip with said cells.

24. The method of claim 23, further comprising the step of utilizing said strip as a planar viewing surface for examination of said cells.

* * * * *